United States Patent
Zheng et al.

(10) Patent No.: US 10,327,739 B2
(45) Date of Patent: Jun. 25, 2019

(54) MEASURING TISSUE SHEAR WAVE PROPERTIES USING ONE EXCITATION PULSE AND EXCITATION PULSES HAVING DIFFERENT WIDTHS AND SHAPES

(71) Applicants: Yi Zheng, Cold Spring, MN (US); Siping Chen, Shenzhen (CN); Tianfu Wang, Shenzhen (CN); Xin Chen, Shenzhen (CN); Haoming Lin, Shenzhen (CN)

(72) Inventors: Yi Zheng, Cold Spring, MN (US); Siping Chen, Shenzhen (CN); Tianfu Wang, Shenzhen (CN); Xin Chen, Shenzhen (CN); Haoming Lin, Shenzhen (CN)

(73) Assignee: Yi Zheng, Cold Spring, MN (US)

( * ) Notice: Subject to any disclaimer, the term of this patent is extended or adjusted under 35 U.S.C. 154(b) by 272 days.

(21) Appl. No.: 15/090,357

(22) Filed: Apr. 4, 2016

(65) Prior Publication Data
US 2017/0367683 A1  Dec. 28, 2017

Related U.S. Application Data

(60) Provisional application No. 62/143,017, filed on Apr. 3, 2015.

(51) Int. Cl.
*A61B 8/08* (2006.01)
*G01S 7/52* (2006.01)
*G01S 7/62* (2006.01)

(52) U.S. Cl.
CPC ............ *A61B 8/485* (2013.01); *A61B 8/5223* (2013.01); *G01S 7/52022* (2013.01);
(Continued)

(58) Field of Classification Search
CPC ... A61B 8/485; A61B 8/5223; G01S 7/52022; G01S 7/52038; G01S 7/52042; G01S 7/52071; G01S 7/6263
See application file for complete search history.

(56) References Cited

U.S. PATENT DOCUMENTS

| | | | |
|---|---|---|---|
| 10,172,527 B2 * | 1/2019 | Pernot | A61B 5/021 |
| 2014/0094702 A1 * | 4/2014 | Kim | G01N 29/0654 |
| | | | 600/438 |

OTHER PUBLICATIONS

Sinkus, et al. "Nonlinear viscoelastic properties of tissue assessed by ultrasound", IEEE Transactions on Ultrasonics Ferroelectrics and Frequency Control. vol. 53, No. 11 (pp. 2009-2017). 2006 (Year: 2006).*

* cited by examiner

*Primary Examiner* — Michael T Rozanski
(74) *Attorney, Agent, or Firm* — Merchant & Gould P.C.

(57) ABSTRACT

Ultrasound radiation using a single tone burst pulse is applied to a selected location in a tissue region. The induced shear wave is detected in the region and its spectral distribution is calculated and analyzed. This detection may be repeated with other excitation pulses having different widths or different shapes at the same location. The spectral analysis of the detected shear wave is performed according to a nonlinear shear model for solving nonlinearity and viscoelasticity of the tissue at a single location. The detection location can be at one point at a time for imaging two-dimensional or three-dimensional tissue nonlinearities and shear wave properties including nonlinear magnitude variations, nonlinear phase variations, nonlinear coefficients, and viscoelasticity. The induced shear wave are detected at multiple locations along the shear propagation directions for calculating different shear group velocities and different
(Continued)

shear phase velocities using different excitation pulses, and calculating nonlinearity and viscoelasticity.

15 Claims, 10 Drawing Sheets

(52) U.S. Cl.
CPC ...... *G01S 7/52038* (2013.01); *G01S 7/52042* (2013.01); *G01S 7/6263* (2013.01); *G01S 7/52071* (2013.01)

MEASURING TISSUE SHEAR WAVE PROPERTIES USING ONE EXCITATION PULSE AND EXCITATION PULSES HAVING DIFFERENT WIDTHS AND SHAPES

CROSS-REFERENCE TO RELATED APPLICATIONS

This application claims the benefit of U.S. Provisional Patent Application No. 62/143,017, filed Apr. 3, 2015. The disclosure of U.S. Provisional Patent Application No. 62/143,017 is incorporated herein by reference.

BACKGROUND

Quantitative ultrasound elastography measures tissue viscoelasticity by applying ultrasound radiation force to a tissue region, measuring the propagation properties of induced shear waves, such as displacements and propagation velocities (group velocity or phase velocity), and calculating viscoelasticity of the tissue. These technologies include ultrasound vibrometry (U.S. Pat. Nos. 7,753,847, 7,785,259, 8,659,975, 8,602,994), ARFI (US 20050215899), Supersonic shear Imaging (SSI) and Shear wave Spectroscopy (SWS) (U.S. Pat. No. 8,150,128), and other similar techniques such as Shear Wave Elasticity Imaging (SWEI), Spatially Modulated Ultrasound Radiation Force (SMURF), Crawling Wave Sonography (CWS).

Above said methods assume that tissue response to excitation pulses are linear, so that the measurements of tissue property such as group velocity and phase velocity of shear wave are independent to excitation pulse widths and shapes, as the said velocities are used to calculate the tissue viscoelasticity for charactering tissue shear property.

Above said methods do not measure tissue nonlinearity, nor consider the impact of the nonlinearity to the accuracy of the estimates of the tissue viscoelasticity.

Above said methods require the detection of shear wave at multiple locations to estimate shear wave velocities in order to calculate the viscoelasticity of tissue.

SUMMARY

This work finds that measured propagation velocities of shear waves are not independent to excitation pulse widths and shapes in biological tissues such as swine livers. It is partially due to the complexity of biological structures of tissue including nonlinearity, anisotropy, and non-uniformity, etc. For a tissue region, this disclosure finds that the measured tissue shear property of the induced shear waves including group velocities and phase velocities are different for different excitation pulses. Thus, the calculated viscoelasticity of the tissue are different for different vibration pulses in the same tissue region. Therefore, the estimated tissue viscoelasticity using the said prior art of elastography is pulse dependent.

This disclosure discloses the method and apparatus to characterize tissue shear property using different vibration pulses having difference widths and shapes.

According to one aspect of this disclosure, the detection location can be at one point at a time for imaging two-dimensional or three-dimensional tissue shear wave property investigated by different excitation pulses. The property includes nonlinear magnitude variations, nonlinear phase variations, and combination parameters based on the responses excited by different pulses, which are related to the tissue shear property and pathological statues.

According to another aspect of this disclosure, the induced shear wave can be also detected at multiple locations in the tissue region for calculating different group velocities and phase velocities using different excitation pulses. For example, excitation pulses having pulse widths of 50 μs and 100 μs are used to induce shear waves, respectively. This disclosure estimated the group velocities and phase velocities of shear wave induced by the said two different excitation pulses. The measured velocities and its dispersion with different pulses are used to characterize tissue shear properties, which are used to characterize different types of tissue and pathological statues of the tissues.

Another aspect of this disclosure discloses a method to measure tissue nonlinearity by using a single pulse or a sequence of the same pulses for a measurement, while as the measurement is repeated for different pules having different widths and shapes.

Another aspect of this disclosure is to correct the viscoelasticity measured by the said priori elastography technologies, by providing a standard of specified pulse widths.

DETAILED DESCRIPTION

Figure 1:
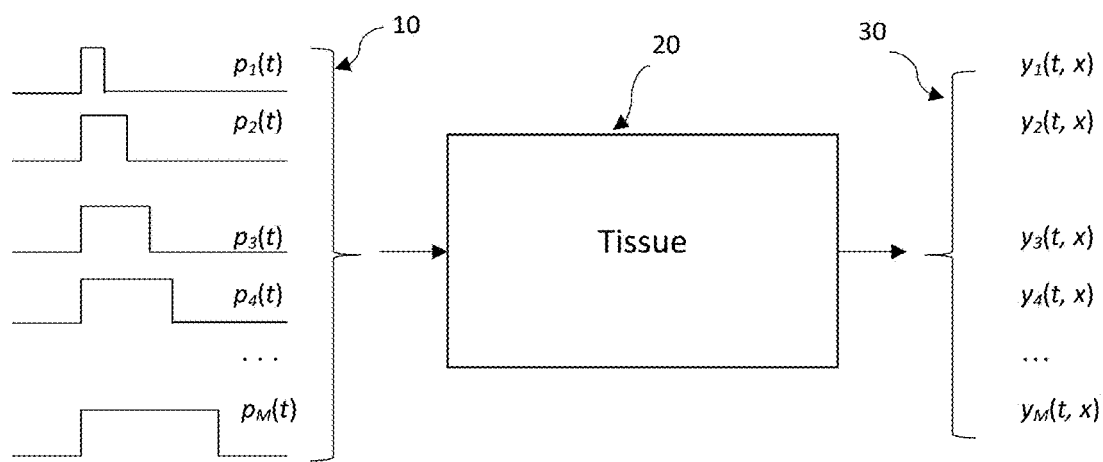
FIG. 1 shows a radiation force pi(t) generated by one of pulses having different widths is applied to a tissue region to induce a shear wave yi(t, x), i=1, 2, ... M, and x is a location according to an aspect of the disclosure. The process is repeated for another pulse till all shear waves induced by pulses having different widths are measured for estimating the tissue shear property including nonlinearity.

When ultrasound radiation force is applied to viscoelastic tissue, the induced tissue shear motion in a tissue region can be described by Newton's second law of motion:

$$\sum_{k=1}^{3} \frac{\partial \sigma_{jk}}{\partial x_k} = \rho \frac{\partial^2 d_j}{\partial t^2} (j = 1, 2, 3) \tag{1}$$

where $(x_1, x_2, x_3)$ are Cartesian coordinates, $(\sigma_{11}, \sigma_{12}, \sigma_{13})$ are $x_1$, $x_2$, $x_3$-components of the stress per unit cross the $x_2$-$x_3$ plane, analogous to other components, $d_j$ is the displacement of the motion in $x_j$ direction, $\rho$ is density. This equation states that the net internal forces per unit area are derivatives of the stress tensors in space, and the net forces induce the accelerated motions at location $(x_1, x_2, x_3)$.

The wave propagation speeds of the wave components described by (1) are useful for studying the mechanical properties of the tissue, such as shear elasticity and viscosity of tissue.

Considering a harmonic motion of the shear wave of which the tissue displacement is parallel to the compressional wave front and the propagation direction is perpendicular to the compressional wave front in an isotropic viscoelastic medium, (1) is reduced to:

$$\frac{\partial^2 d_1}{\partial x_k^2} + h^2 d_1 = 0, \forall k = 2 \text{ or } 3 \tag{2}$$

where $d_1$ is the displacement of the harmonic motion, $x_k$ is in the direction that is perpendicular to the wave front of the compressional wave, h is the wave number of the shear wave in the $x_k$ direction. The solution of (2) for a motion having only one single harmonic is:

$$d_1(x,t) = \text{Re}\{De^{j(\omega t - hx)}\} De^{-h_I x} \cos(\omega t - h_r x) \tag{3}$$

where $h_r$ and $h_I$ are real and imaginary parts of h, respectively, D is the initial amplitude of the tissue displacement, $\omega$ is the angular frequency of the harmonic motion, and x is the travel distance. The velocity of the shear wave can be obtained by taking time derivative of $(\omega t - h_r x)$, which is:

$$v_s(t) = \frac{\omega}{h_r} \tag{4}$$

The said priori methods measure the velocity $v_s(\omega)$ and solve the tissue viscoelasticity that is related to $h_r$, which is dependent to the tissue viscoelasticity model. Tissue viscoelasticity can be modelled by many different models. The simplest one is:

$$\sigma(t) = \mu_1 \varepsilon(t) \tag{5}$$

where $\sigma$ is stress, $\varepsilon$ is strain, $\mu_1$ is called elasticity. Thus, $$v_s(\omega) = \frac{\omega}{h_r} = \sqrt{\frac{\mu_1}{\rho}} \tag{6}$$

where $\rho$ is the density of tissue. Another popular model with one additional element for viscoelastic tissue is called Voigt model:

$$\sigma(t) = \mu_1 \varepsilon(t) + \mu_2 \frac{d\varepsilon(t)}{dt} \tag{7}$$

where $\mu_2$ is called viscosity. For a harmonic motion:

$$\sigma/\varepsilon = \mu_1 + j\omega\mu_2 \tag{8}$$

For the Voigt medium:

$$h = \sqrt{\rho\omega^2/(\mu_1 + i\omega\mu_2)} \tag{9}$$

Thus, the phase velocity of the shear wave in Voigt tissue:

$$v_s(\omega) = \frac{\omega}{h_r} = \sqrt{\frac{2(\mu_1^2 + \omega^2 \mu_2^2)}{\rho\left(\mu_1 + \sqrt{\mu_1^2 + \omega^2 \mu_2^2}\right)}} \tag{10}$$

It can be showed that the amplitude of the shear wave in distance is also a function of tissue viscoelasticity, and the similar equations to (6) and (10) can be found that relate amplitude attenuations to the viscoelasticity.

For other tissue viscoelastic models, the velocity related to wave number h and viscoelasticity can be found by using (4). They can be found in literatures and are not listed here.

The priori technologies calculate viscoelasticity based on the velocities or amplitudes of the induced shear waves over a distance. Thus, the detection of shear wave at multiple locations are required. This limits its applications for tissue points and tissue imaging.

In theory, the phase velocities and group velocity of shear wave in the tissue region represent tissue property, and they should not be dependent to the excitation pulses, which is true if the tissue response to the radiation force is linear. In this case, for Voigt tissue, the velocity is given by (10); for tissue having only elasticity, the velocity is given by (6). The shape of the applied radiation force may be changed over a distance due to attenuation, but this change has no impact to propagation phase velocity.

This work finds that the propagation velocities (both group and phase velocities) and the shapes of the induced shear waves may be changed in the tissue. These changes are functions of both the tissue property and the shapes of applied radiation forces. When excitation pulses are used to generate the ultrasound radiation force in a complex tissue region which may be nonlinear, the pulse width has impact to the measured propagation velocities. Thus, the calculated viscoelasticity is not unique as described by (6) and (10) and other equations. This situation is also true for the radiation force generated by continue waves or periodic pulse sequences.

For an example, assume that the induced shear wave has two harmonics ($\omega_2 = 2\omega_1$) at location x:

$$d(x,t) = D(\omega_1)e^{-h_I(\omega_1)x} \cos(\omega_1 t - h_r(\omega_1)x) + D(\omega_1)e^{-h_I(\omega_1)x} \cos(\omega_1 t - h_r(\omega_1)x) \tag{11}$$

Further assume that the tissue is nonlinear and its transfer function is modeled by a square term at distance $x + \Delta x$:

$$[D(\omega_1)e^{-h_I(\omega_1)(x+\Delta x)} \cos(\omega t - h_r(\omega_1)(x+\Delta x)) + D(\omega_2)e^{-h_I(\omega_1)(x-\Delta x)} \cos(\omega t - h_r(\omega_2)(x+\Delta x))]^2 \tag{12}$$

This quadrature term produces new frequency components of $(\omega_2 - \omega_1) = \omega_A$ and $(\omega_2 + \omega_1) = \omega_B$. Thus, the harmonic of $\omega_A$ at x+Δx includes phase information of harmonics $\omega_1$ and $\omega_2$ at x, but $\omega_A-\omega_1$. Similarly, the harmonic of $\omega_B$ at x+Δx introduce a new harmonic component at $3\omega_1$. If such harmonic $\omega_B$ exists at the location, it will be modified. Thus, the phase difference used to calculate the velocity does not only depend on the tissue viscoelasticity, but also the nonlinearity of the tissue. As different excitation pulses have different harmonic distributions, the impact the nonlinearity is different to different pulses; thus, the measured velocity does not only depend on the tissue viscoelasticity, but also pulse shapes. This tissue nonlinearity can be measured by the method disclosed in this disclosure.

The general concept of this disclosure to measure the tissue shear nonlinearity and shear viscoelasticity is shown in FIG. 1. One ultrasound excitation pulse (a tone burst), or a pulse sequence, is applied to a tissue region 20 to generate radiation force $p_i(t)$ 10. The pulse or the pulses in a sequence have a prescribed pulse width. The radiation force induced shear wave in the tissue region 20. The shear wave $y_i(t)$ induced by $p_i(t)$ is detected by pulse echo ultrasound. The procedure is repeated for another pulse, till all shear waves 30, $y_1(t)$, $y_2(t)$ $y_3(t)$, . . . $y_M(t)$ induced by $p_1(t)$, $p_2(t)$, $p_3(t)$, . . . , $p_M(t)$ (20) are obtained. The measured shear waves 30 are processed for tissue shear property and non-linearity estimation.

Figure 2:
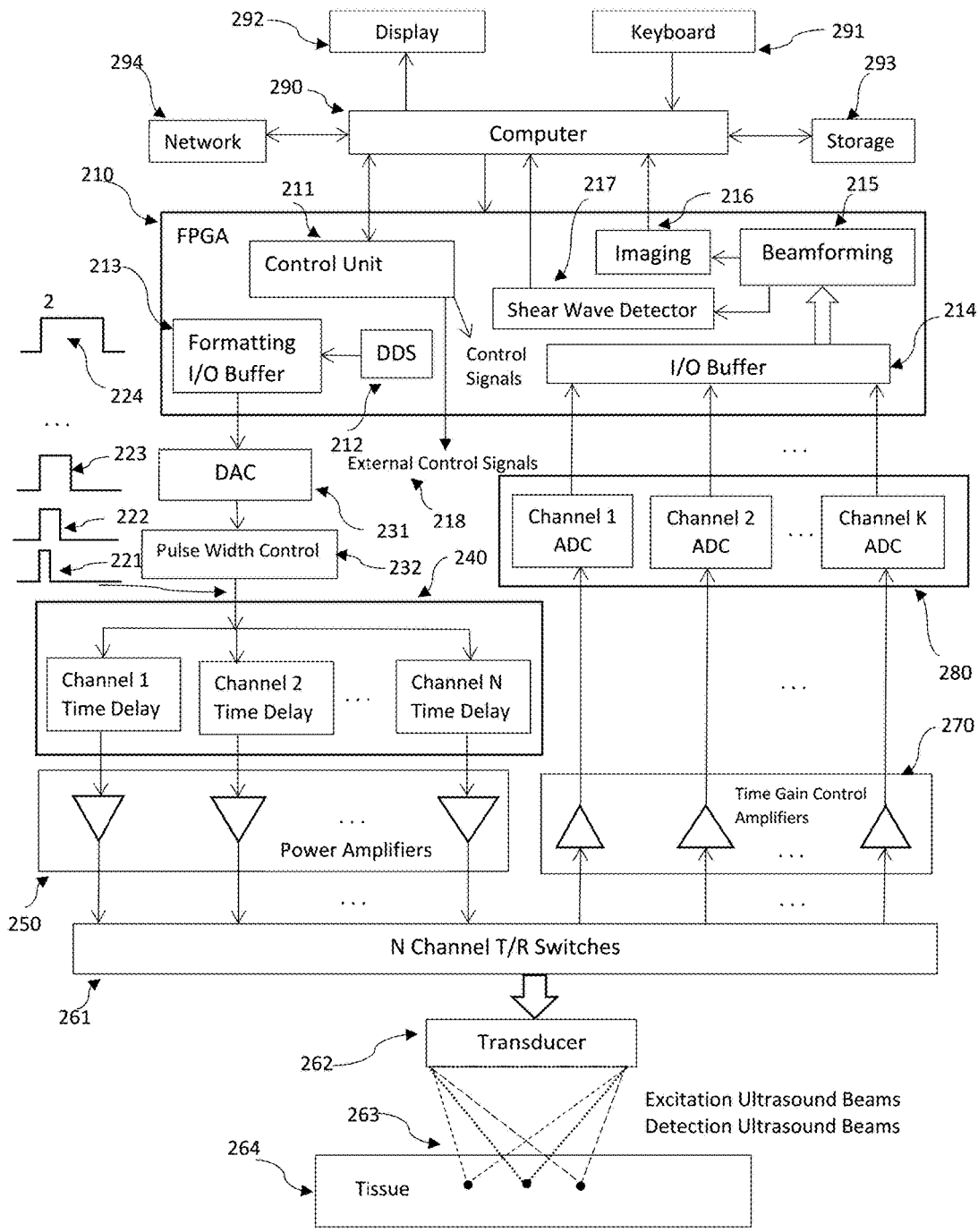
FIG. 2 shows a system diagram of tissue shear property characterization using ultrasound radiation force induced by excitation pulses having different widths and shapes according to an aspect of the disclosure.

The block diagram of ultrasound system to implement this disclosure is shown in FIG. 2. The sinusoidal digital signal is synthesized and generated by a direct digital synthesis (DDS) 212 implemented in a FPGA 210. The frequency of the signal is prescribed and controlled by configuring the DDS 212 using Control Unit 11 and Computer 90. The digital sinusoidal signal is formatted and buffered in 13 and is converted to an analog signal by a digital to analog converter (DAC) 231. DAC 231 outputs the analog signal that has a prescribed center frequency to the pulse with control unit 232. Pulses 221, 222, 223, 224 show the envelopes of the signal at the output of pulse width control unit 232. They are called excitation pulses. Only one excitation pulse or a sequence of excitations pulse having the same pulse width are generated to induce shear wave in a tissue region. Beamforming circuit 240 distributes the excitation pulse to multiple channels having different time delay for transmission focus. The excitation pulses are amplified by the power amplifiers 250 and applied to ultrasound transducer via T/R switches 261. Shear wave is induced in a tissue region 264 by ultrasound radiation force generated by the excitation pulses.

Using the pulse echo ultrasound method which has been reported in many literatures, the shear wave can be measured. With proper pulse widths, amplifier gains, and timing control, the same transmitting circuits shown FIG. 2, which is discussed above, can be used to generate detection pulses. Periodic detection pulses are transmitted to a detection location in tissue region 264. The echoes of the detection pulses are received by multiple channels of the ultrasound transducer 262, passed through the T/R switch 261, amplified by time-gain control amplifiers, and digitized by the ADC 280. The digitized echoes are processed by beamforming unit 215 in FPGA 210. The detected RF signal representing the shear wave is received by shear wave detector 217, which demodulates the RF signal and extracts the motion representing the shear wave. The shear wave detection is documented by many literatures including the prior art of U.S. Pat. No. 7,785,259. The detected shear wave including amplitudes, group velocity, and phase velocity are transmitted to computer 290.

Above transmission and detection processes are repeated for another pulse having another pulse width, till all shear waves induced by pulses having different pulse width are measured for tissue shear property characterization.

Above ideal has been experimentally illustrated by investigating shear wave speeds of a swine liver embedded in a gelatin phantom using an ultrasound experiment system. The ultrasound excitation pulses had a center frequency of 4.1 MHz with pulse widths of 10 μs, 20 μs, . . . , 100 μs. The receiving transducer had a center of 6.25 MHz. The group velocities and phase velocities for each excitation pulse were measured. The experiments were repeated ten times for each pulse in two regions of the liver to find the averages and standard deviations (SD) of the group velocities and phase velocities.

Figure 3:
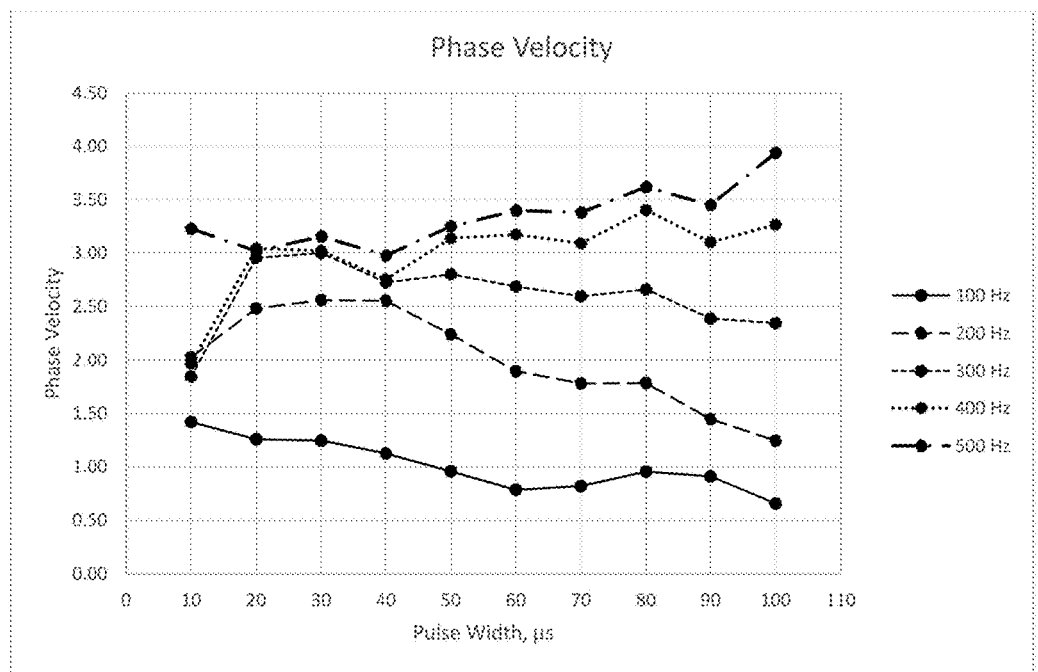
FIG. 3 shows phase velocities of shear waves in a swine liver phantom according to an aspect of the disclosure. It shows that the phase velocity of the induced shear wave at a given frequency is not a constant, but varies with the pulse width. This dispersive property of phase velocity with different pulse widths represents tissue pathological statues.

FIG. 3 shows the phase velocities of five harmonics of shear waves in the liver. The shear waves are induced by the pulses having different pulse widths from 10 μs to 100 μs for 100 Hz and 200 Hz, and 500 Hz. It shows that the phase velocity of the induced shear wave at a given frequency is pulse width dependent, not a constant. The different phase velocities produce different viscoelasticity estimates, as indicated by equation (10). On other hand, the dispersive property of the phase velocities with different pulse widths represents the tissue pathological property. FIG. 3 also shows that the differences of the phase shifts due to difference of the pulse widths is larger in the lower frequency range, which is the important frequency range for ultrasound induced shear waves.

Figure 4:
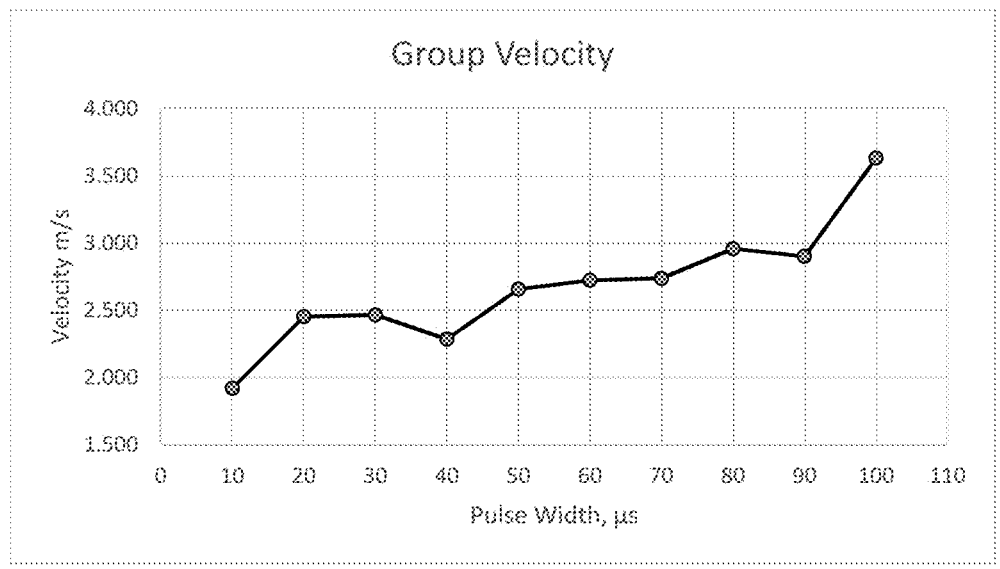
FIG. 4 shows group velocities of shear waves in a swine liver phantom according to an aspect of the disclosure. It shows that the group velocity of the induced shear wave is not a constant, but varies with the pulse widths. This dispersive property of group velocity with different pulse widths represents tissue pathological statues.
Figure 5:
FIG. 5 show estimated elasticities of a swine liver phantom. It shows that the estimated elasticity of a swine liver is not a constant, but varies with the pulse width according to an aspect of the disclosure. This dispersive property of estimated elasticity with different pulse widths represents tissue pathological statues.
Figure 6:
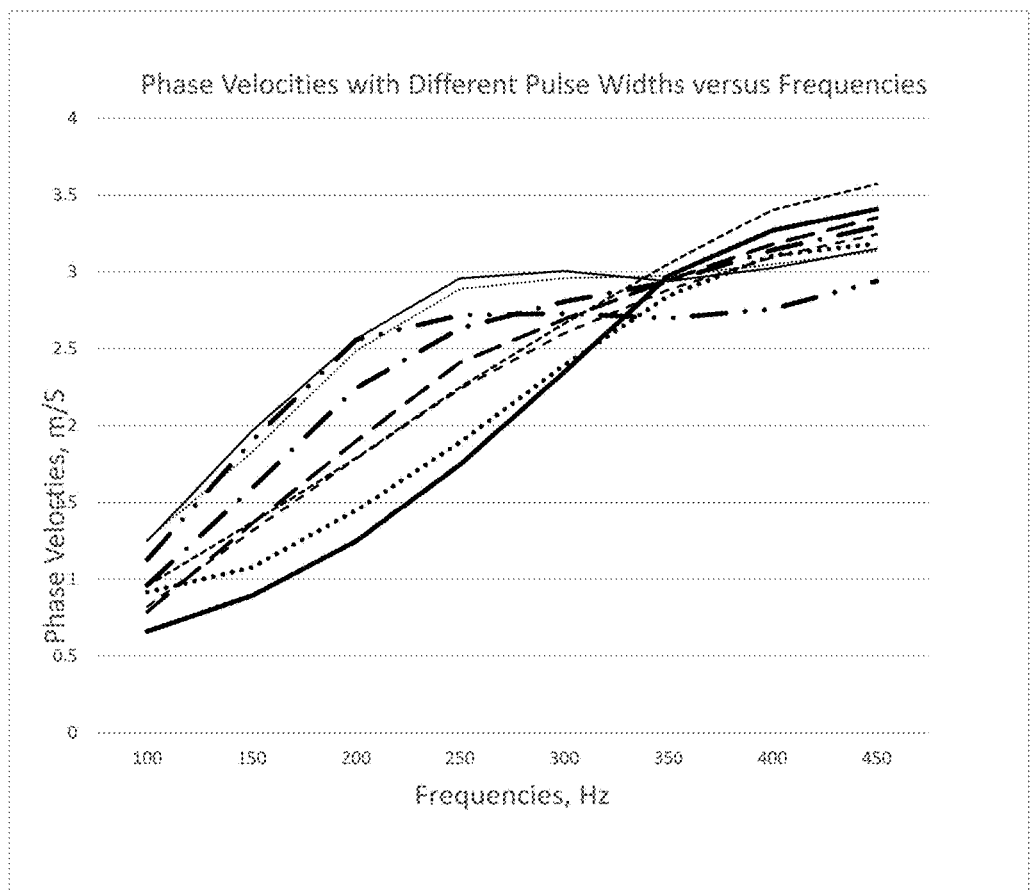
FIG. 6 show estimated phase velocities of a swine liver phantom versus frequency according to an aspect of the disclosure. It shows that the estimated elasticity of a swine liver is not a constant at a frequency, but varies with the pulse widths.

FIG. 4 shows the group velocities of shear waves in the swine liver phantom. It shows that the group velocity of the induced shear wave is not a constant, but varies with the pulse width. The different group velocities lead to different tissue elasticity estimates as shown in FIG. 5, which is obviously not a constant for different excitation pulses. This dispersive properties of group velocities and estimated elasticities with different pulse width represent tissue pathological statues. The phase velocities measured with different excitation pulses are also shown in FIG. 6, which shows the velocities versus frequencies. In the prior art, the velocity has a single value at a frequency. In this case, the velocities of shear wave induced by the wider pulses have lower values in lower frequencies than those with narrower pulses, the velocities of shear wave induced by the wider pulses have higher values in higher frequencies than those with narrower pulses.

According to one aspect of this disclosures is to measure tissue shear properties using different pulses. The shear group velocities, shear phase velocities, and viscoelasticity measured with different excitation pulses are used to characterize the tissue shear property and tissue pathological statues. The distribution of the phase velocities versus different pulse widths is illustrated in FIG. 3. The distribution of the group velocities versus different pulse widths is illustrated in FIG. 4. The distribution of the elasticity calculated from the measured group velocities versus different pulse widths is illustrated in FIG. 5. The phase velocity versus frequencies using different excitation pulses are shown in FIG. 6.

According to another aspect of this disclosure is to use the averaged value of all measurements with different pulse widths to characterize the tissue pathological statues.

According to another aspect of this disclosure is to use the measurements with a selected pulse width to characterize the tissue pathological statues with a labeled pulse width.

According to another aspect of this disclosure is to model and measure the nonlinear tissue responses using different excitation pulses. If tissue responses to different excitation pulses are linear, assumed in the prior art of elastography, shear wave velocities are independent to different excitation pulses. However, as illustrated in FIGS. 3, 4, and 5, the shear velocities are pulse dependent. This phenomenon can be modeled by nonlinear models.

For the Voigt tissue that has a linear response to an applied force, $$Y_i(\omega) = \frac{P_i(\omega)}{A_0(\mu_1 + j\omega\mu_2)} = H(\omega)P_i(\omega)/A_0, \quad (13)$$

for
$i = 1, 2, \ldots, M,$ where $P_i(\omega)$ is Fourier transform of the radiation force that is proportional to the excitation pulses, $Y_i(\omega)$ is Fourier transform of shear wave $y_i(t)$, $H(\omega)$ is a transfer function, $A_0$ represents a transfer efficiency of the applied radiation force to the detection location for the shear wave. (13) can be rearranged as:

$$\frac{P_i(\omega)}{Y_i(\omega)} = A_0(\mu_1 + j\omega\mu_2) = R_i(\omega) + jI_i(\omega), \quad (14)$$

for $i = 1, 2, \ldots, M.$ $$\frac{I_i(\omega)}{R_i(\omega)} = \frac{\omega\mu_2}{\mu_1}, \quad (15)$$

for $i = 1, 2, \ldots, M.$

For the linear tissue, values obtained by (14) and (15) are the same for all different radiation force $p_i(t)$ $A_0$ is unknown, because it dependents on locations in tissue and transmitting transducer and power etc. Thus, the $\mu_1$ and $\mu_2$ in (14) and (15) cannot be calculated with the measurement of $y_i(t)$ at a tissue location. The prior art of elastography requires measurements from two locations to estimate the group velocity or phase velocities so that (6) or (10) can be used to calculate $\mu_1$ and $\mu_2$.

For the nonlinear response, the Fourier transforms of tissues responses are:

$$Y_i(\omega) = \frac{1}{A_0}[H(\omega)P_i(\omega)]^\alpha, \quad (16)$$

for $i = 1, 2, \ldots, M,$ where $\alpha$ is defined as the shear nonlinear exponent coefficient (SNEC). For the Voigt tissue, $$Y_i(\omega) = \frac{P_i^\alpha(\omega)}{A_0(\mu_1 + j\omega\mu_2)^\alpha}, \quad (17)$$

for $i = 1, 2, \ldots, M$

As shown in (17) the linear relationship between $A_0$ and $(\mu_1+j\omega\mu_2)$ is no longer valid. Thus, the four unknown ($A_0$, $\mu_1$, $\mu_2$, and $\alpha$) at the right hand side of (17) are independent each other and can be numerically solved by fitting with the $Y_i(\omega)$ and $P_i(\omega)$ over a frequency range. $Y_i(\omega)$ is given by the Fourier transform of the shear wave measurements. Recognizing the excitation pulse is rectangular, the relationship between the radiation force and the excitation pulse is a scaling factor. Thus, $P_i(\omega)$ can be given by the Fourier transform of the excitation pulse, as the scaling factor is included in $A_0$.

For example, a tone burst (M=1) with a certain width is transmitted to induce a shear wave in a tissue region. The shear wave is detected at a location that is near or at the location where the radiation force is applied. The shear wave at this location is detected by pulse echo ultrasound and the Fourier analysis is applied to the detected shear wave. Let $\omega$ increases from 1 Hz to 800 Hz with a step size of 1 Hz, there are 2×800=1600 complex data of $Y_i(\omega)$ and $P_i(\omega)$ for fitting (17) and solving the four unknown variables: $A_0$, $\mu_1$, $\mu_2$, and $\alpha$. In this case, a single transmission of vibration pulse is transmitted to generate the shear wave and viscoelasticity is estimated at a selected location.

When the number M of different pulses increases, the numerical fitting is enhanced and the reliability of the estimates is increased. For example, select M=8, so that the pulse widths are 25, 50, 75, . . . , 200 μs, with a step size of 25 μs. Thus, there are 2×800×8=12,800 data available to fit (17) for unknown variable of $A_0$, $\mu_1$, $\mu_2$, and $\alpha$. The frequency range and the pulse width in this example are for illustration purpose, which are selected and prescribed for different applications.

According to another aspect of the disclosure, the viscoelasticity parameters ($\mu_1$, $\mu_2$)) of tissue can be estimated by the measurements of shear wave at one location, which is different than the prior art of elastography.

According to another aspect of the disclosure, the measured viscoelasticity of every location in a tissue region can be used to form a two-dimensional image or three-dimensional image, which presents the viscoelasticity of the tissue region.

According to another aspect of this disclosure, the accuracy and reliability of the estimates of viscoelasticity ($\mu_1$, $\mu_2$)) should be improved as the number of different pulses increases from M=1 to a large number.

According to another aspect of this disclosure, tissue is modeled by a general form that includes linear and nonlinear components of tissue:

$$Y_i(\omega) = A_1\{H(\omega)P_i(\omega) + \beta[H(\omega)P_i(\omega)]^\alpha\}, \text{ for } i=1,2,\ldots,M. \quad (18)$$

where $A_1$ is an inverse of $A_0$. For the Voigt tissue, $$Y_i(\omega) = A_1\{P_i(\omega)/(\mu_1+j\omega\mu_2) + \beta P_i^\alpha(\omega)/(\mu_1+j\omega\mu_2)^\alpha\}, \text{ for } i=1,2,\ldots,M, \quad (19)$$

where $\beta$ is defined as shear nonlinear content coefficient (SNCC) to represent the content of the nonlinearity of the tissue. Because the tissue responses are not completely linearly changed in the frequency range, five parameters $A_0$, $\mu_1$, $\mu_2$, $\alpha$, and $\beta$ are mutually independent. Therefore, the Fourier transforms of the pulses and detected shear wave induced by either one single pulse or multiple pulses or different pulses can be applied to fit (19) for solving unknown $A_0$, $\mu_1$, $\mu_2$, $\alpha$, and $\beta$.

Figure 7:
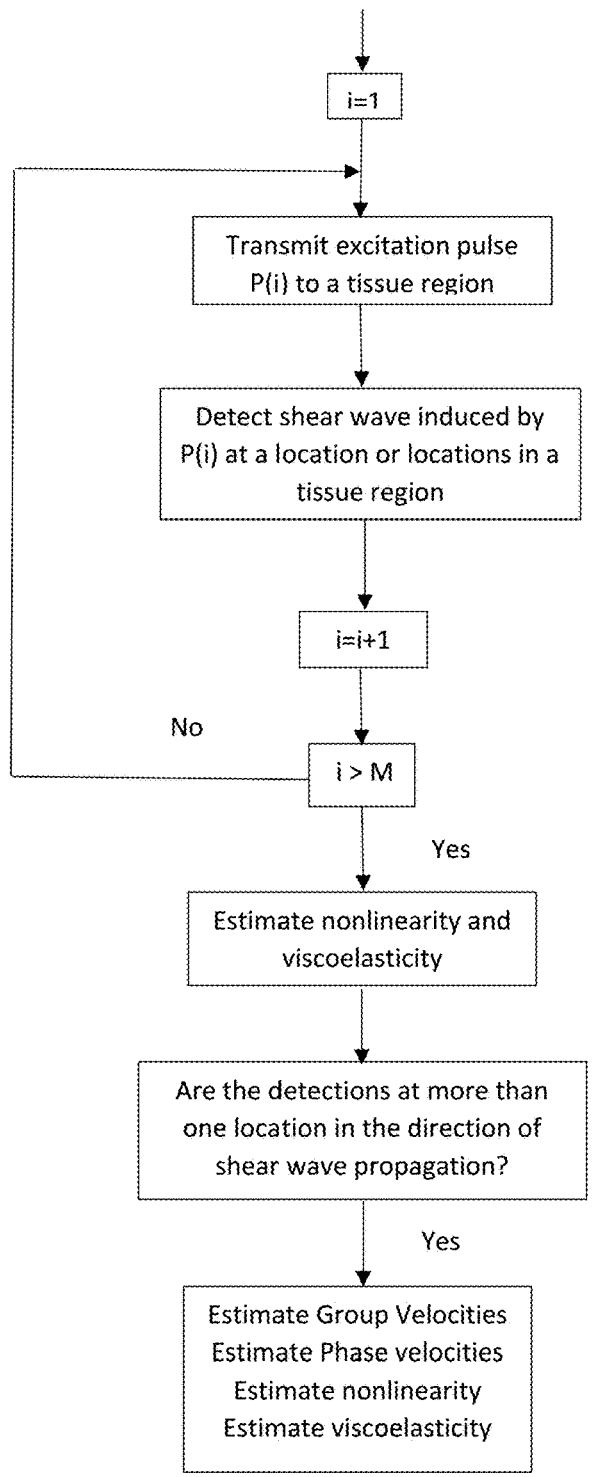
FIG. 7 shows a procedure to measure tissue nonlinearity, viscoelasticity, and shear velocities by using a single pulse or different excitation pulses at one or more locations according to an aspect of the disclosure.

FIG. 7 shows the key procedure to measure tissue nonlinearity, viscoelasticity, shear motion, and shear velocities by using a single pulse or different excitation pulses at one or more locations.

Certain methods and devices disclosed in this disclosure have several important advantages:
1. The estimation of tissue viscoelasticity requires only the shear wave measured from one location in a tissue region.
2. The estimate of tissue viscoelasticity can be done with a single transmission of an excitation pulse.

3. The multiple transmission of the excitation pulses enhance the reliability of the estimates.
4. The transmission of the multiple excitation pulses enhance the accuracy and reliability of the estimates.
5. Quantitative 2D and 3D images for viscoelasticity of each point in a tissue region issue can be obtained.
6. The nonlinear parameter α and β are calculated to characterize tissue shear wave property and pathology statues.
7. Parameter β indicates the linearity level. When β=0.0, only the ratio between elasticity and viscosity can be obtained and measurements at two locations are required for estimating tissue viscoelasticity.
8. The phase shift distribution of shear waves induced by different excitation pulses is a unique tissue mechanical property, which directly represent tissue shear property including the nonlinearity.

As the measurement of shear waves is pulse dependent, one aspect of this disclosure to label viscoelasticity measurements with used pulse width and shapes.

While this disclosure is benefited by the prior art of elastography for the transmitting the ultrasound radiation force and detection of the shear wave using pulse-echo ultrasound, the following aspects of this disclosure are unique.

One of the aspects of this disclosure is to transmit one excitation pulse to a location in a tissue region to induce shear wave, detect the induced shear wave, take Fourier analysis and fit the results with (17) or (19) to estimate shear elasticity, shear viscosity, shear nonlinear coefficient of the tissue at the location. This allows the estimates of viscoelastic parameters without using shear velocities which require measurements of shear waves at two or more locations.

Figure 8:
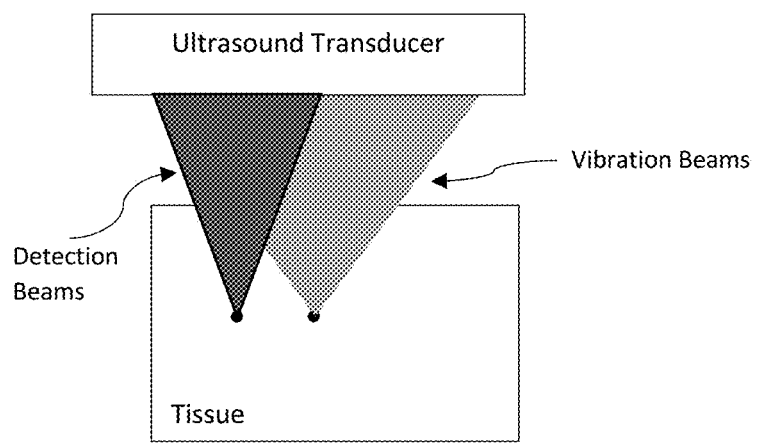
FIG. 8 shows the vibration beams and detection beams aimed at different locations according to an aspect of the disclosure.
Figure 9:
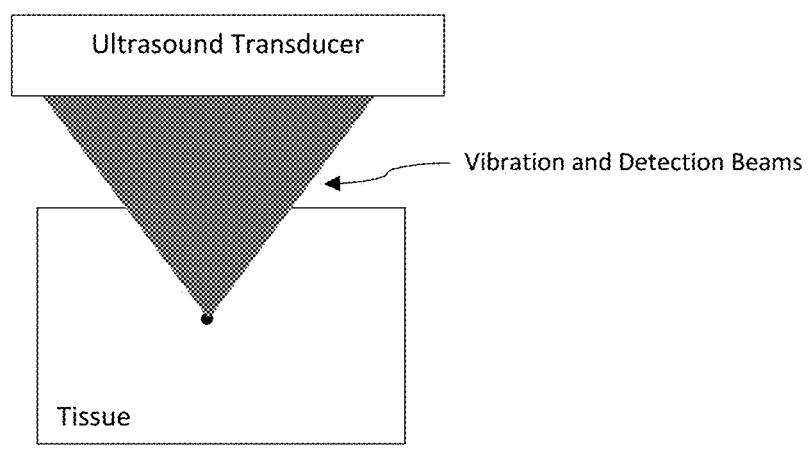
FIG. 9 shows the vibration beams and detection beams aimed at the same location according to an aspect of the disclosure.

Another aspect of this disclosure is to transmit different excitation pulses having different pulse widths to a location in a tissue region to induce shear wave, detect the induced shear wave, take Fourier analysis and fit the results with (17) or (19) to estimate elasticity, viscosity, nonlinear coefficient α and β of the tissue at the location, shown in FIG. 8. The locations of excitation and detections can be the same location as shown in FIG. 9. This allows the estimates of viscoelastic parameters without using shear velocities which require measurements of shear waves at two or more locations.

Figure 10:
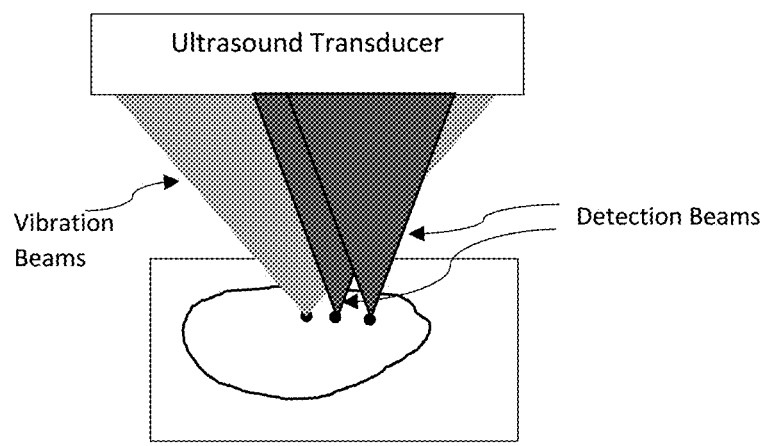
FIG. 10 shows the vibration beams and detection beams are aimed at different locations according to an aspect of the disclosure; detections are done at multiple locations in multiple dimensions in a region.

Another aspect of this disclosure is to form a quantitative viscoelastic and nonlinear coefficients α and β 2D or 3D image of a tissue region as the viscoelasticity of each location in the region is truly independent measured as shown in FIG. 10.

Another aspect of the disclosure is to calculate the difference of phase shifts of shear waves induced by two or more different excitation pulses, and use the difference to characterize tissue shear mechanical property.

Another aspect of this disclosure is to transmit different excitation pulses having different pulse widths to two or more locations in a tissue region to induce shear wave, detect the induced shear wave, take Fourier analysis and fit the results with (17) or (19) to estimate elasticity, viscosity, nonlinear coefficient of the tissue in the region, as shown in FIG. 9.

Another aspect of this disclosure is to transmit different excitation pulses having different pulse widths to two or more locations in a tissue region to induce shear wave, detect the induced shear wave, and use the phase shifts distributions and differences with pulse widths to characterize tissue shear property.

The invention claimed is:

1. A method for measuring a nonlinearity and viscoelasticity of a subject, the method comprising:
    a) generating ultrasound excitation pulses that have prescribed pulse shapes and a center frequency;
    b) applying the ultrasonic excitation pulses using an ultrasonic transducer to a vibration origin in the subject to induce a shear wave motion in the subject;
    c) applying ultrasonic detection pulses to a detection location in the subject to detect the shear wave motion;
    d) performing spectral analysis of the detected shear wave motion and the excitation pulses;
    e) determining the nonlinearity of the subject at the detection location based at least in part on the spectral analysis;
    f) determining the viscoelasticity of the subject at the detection location based at least in part on the nonlinearity using a nonlinear model.

2. The method as recited in claim 1 wherein the excitation pulses are gated tone burst pulses having a prescribed frequency and different prescribed numbers of periods and different pulse widths.

3. The method as recited in claim 1 wherein the excitation pulses are periodical pulses with a prescribed period and a prescribed duty cycle.

4. The method as recited in claim 1 wherein the determining the viscoelasticity of the subject includes determining elasticity and viscosity of the subject.

5. The method as recited in claim 4 wherein the elasticity at multiple locations of multiple dimensions of the subject is color coded for displaying a nonlinearity image of the subject.

6. The method as recited in claim 1 wherein the determining nonlinearity of the subject includes determining nonlinear coefficient SNEC, α, by fitting shear wave measurements to $$Y_i(\omega) = \frac{P_i^\alpha(\omega)}{A_0(\mu_1 + j\omega\mu_2)^\alpha},$$

where α is the shear nonlinear exponent coefficient (SNEC), $P_i(\omega)$ is Fourier transform of the excitation pulses, $Y_i(\omega)$ is Fourier transform of shear wave $y_i(t)$, $H(\omega)$ is a transfer function, $A_0$ is a scaling constant, $\mu_1$ is elasticity of the subject, $\mu_2$ is viscosity of the subject.

7. The method as recited in claim 1 wherein the determining nonlinearity of the subject includes determining nonlinear coefficients SNEC, α and SNCC, β, by fitting shear wave measurements to $Y_i(\omega) = A_1\{P_i(\omega)/(\mu_1+j\omega\mu_2)+\beta P_i^\alpha(\omega)/(\mu_1+j\omega\mu_2)^\alpha\},$ where α is the shear nonlinear exponent coefficient (SNEC), β is defined as the shear nonlinear content coefficient (SNCC), $P_i(\omega)$ is Fourier transform of the excitation pulses, $Y_i(\omega)$ is Fourier transform of shear wave $y_i(t)$, $H(\omega)$ is a transfer function, $A_1$ is a scaling constant, $\mu_1$ is elasticity of the subject, and $\mu_2$ is viscosity of the subject.

8. The method as recited in claim 1 wherein the determining nonlinearity of the subject includes determining a distribution of phase shifts of shear waves versus excitation pulse widths.

9. The method as recited in claim 1 wherein the determining nonlinearity of the subject includes determining differences of phase shifts of shear waves induced by difference excitation pulses versus different frequencies.

10. The method as recited in claim 1 wherein the determining nonlinearity of the subject includes determining a distribution of group shifts of shear waves versus excitation pulse widths.

11. The method as recited in claim 1 wherein the determining nonlinearity of the subject includes determining differences of group shifts of shear waves induced by difference excitation pulses versus different frequencies.

12. The method as recited in claim 1 wherein the nonlinearity at multiple locations of multiple dimensions of the subject is color coded for displaying a nonlinearity image of the subject.

13. The method as recited in claim 1 wherein the viscoelasticity are labeled by pulse widths.

14. The method as recited in claim 1 wherein the nonlinearity are labeled by pulse widths.

15. A method for measuring a nonlinearity and viscoelasticity of a subject, the method comprising:

a) generating an ultrasound excitation pulse having a prescribed pulse shape and a center frequency;

b) applying the ultrasonic excitation pulse using an ultrasonic transducer to a vibration origin in the subject to induce a shear wave motion in the subject;

c) applying ultrasonic detection pulses to a detection location in the subject to detect the shear wave motion;

d) performing spectral analysis of the detected shear wave motion and the excitation pulse;

e) determining the nonlinearity of the subject at the detection location based at least in part on the spectral analysis;

f) determining the viscoelasticity of the subject at the detection location based at least in part on the nonlinearity using a nonlinear model.

* * * * *